(12) United States Patent  
Topp et al.

(10) Patent No.: US 9,724,532 B2
(45) Date of Patent: Aug. 8, 2017

(54) SECURING A TMS COIL TO THE PATIENT'S HEAD

(71) Applicant: University of Florida Research Foundation, Incorporated, Gainesville, FL (US)

(72) Inventors: Eric L. Topp, Gainesville, FL (US); Carolynn Patten, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 536 days.

(21) Appl. No.: 14/160,584

(22) Filed: Jan. 22, 2014

(65) Prior Publication Data

US 2015/0202453 A1    Jul. 23, 2015

(51) Int. Cl.
*A61N 1/00* (2006.01)
*A61N 2/00* (2006.01)
*A61N 2/02* (2006.01)

(52) U.S. Cl.
CPC ............... *A61N 2/006* (2013.01); *A61N 2/02* (2013.01); *A61N 2/002* (2013.01)

(58) Field of Classification Search
CPC ........... A61N 2/006; A61N 2/002; A61N 2/02
USPC ...................................................... 600/9–15
See application file for complete search history.

(56) References Cited

U.S. PATENT DOCUMENTS

| 4,343,047 A * | 8/1982 | Lazowski ............ A42B 3/125 2/411 |
| 5,121,756 A | 6/1992 | Koledin |
| 6,357,054 B1 * | 3/2002 | Bainbridge .......... A41D 13/015 2/267 |
| 6,374,439 B2 | 4/2002 | Heimbrock |
| 2003/0220673 A1 * | 11/2003 | Snell ........................ A61N 1/08 607/60 |
| 2005/0025956 A1 * | 2/2005 | Bainbridge ........ A41D 31/0044 428/317.3 |
| 2005/0148808 A1 * | 7/2005 | Cameron ............. A61G 15/125 600/13 |
| 2007/0106170 A1 * | 5/2007 | Dunseath, Jr. ....... A61B 5/0478 600/544 |
| 2008/0224808 A1 * | 9/2008 | Ghiron ................... A61N 2/006 335/300 |
| 2009/0099473 A1 * | 4/2009 | Dunseath ............. A61B 5/0478 600/544 |
| 2009/0234243 A1 * | 9/2009 | Schneider .......... A61B 5/04009 600/544 |
| 2010/0113959 A1 | 5/2010 | Pascual-Leone |

(Continued)

*Primary Examiner* — Navin Natnithithadha
*Assistant Examiner* — Sunita Reddy
(74) *Attorney, Agent, or Firm* — Alston & Bird LLP

(57) ABSTRACT

A helmet is used to detachably secure a TMS coil to the head of a patient. The helmet has a flexible sack containing a multiplicity of beads and also has a valve that permits air to enter and to be withdrawn from the interior volume of the sack. The handle of the TMS coil is inserted into the helmet, and the helmet is placed upon the head of a patient. Withdrawing air from the interior volume of the sack through the valve causes the sack to shrink and compresses the beads into a compact mass that conforms to the shape of the patient's head. Maintaining the vacuum causes the sack to retain its shape, making it possible to hold the helmet and TMS coil in proper position during a TMS study.

14 Claims, 5 Drawing Sheets

(56) References Cited

U.S. PATENT DOCUMENTS

| | | | |
|---|---|---|---|
| 2010/0173116 A1* | 7/2010 | Bainbridge | A41D 31/0044 428/72 |
| 2011/0270345 A1* | 11/2011 | Johnston | A61N 1/36025 607/45 |
| 2014/0213874 A1* | 7/2014 | Tong | A61B 5/6803 600/383 |
| 2014/0276182 A1* | 9/2014 | Helekar | A61B 5/6803 600/544 |
| 2014/0316367 A1* | 10/2014 | Zugates | A61L 24/0015 604/500 |

* cited by examiner

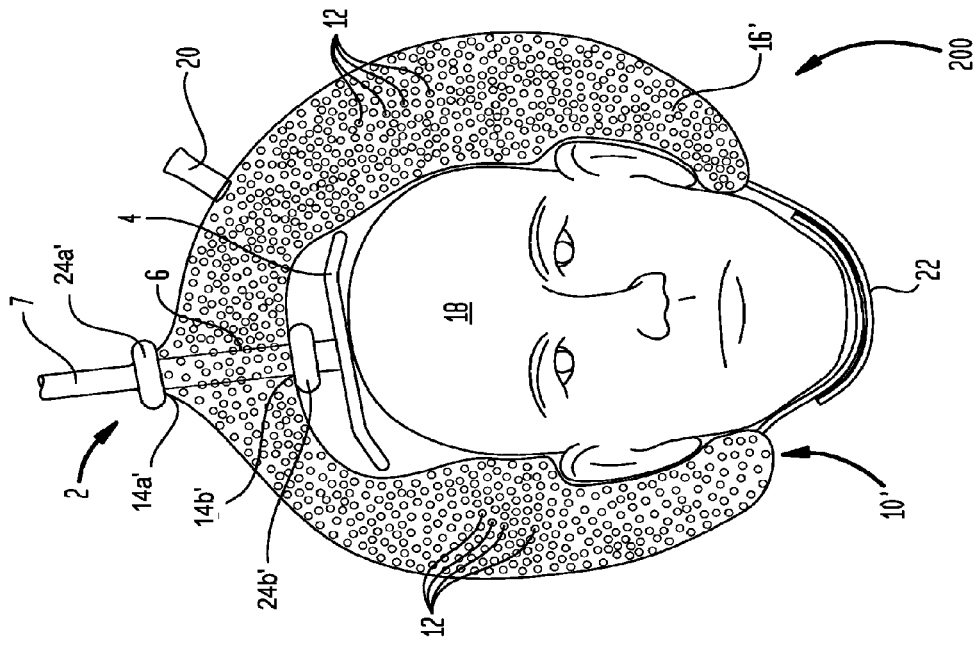
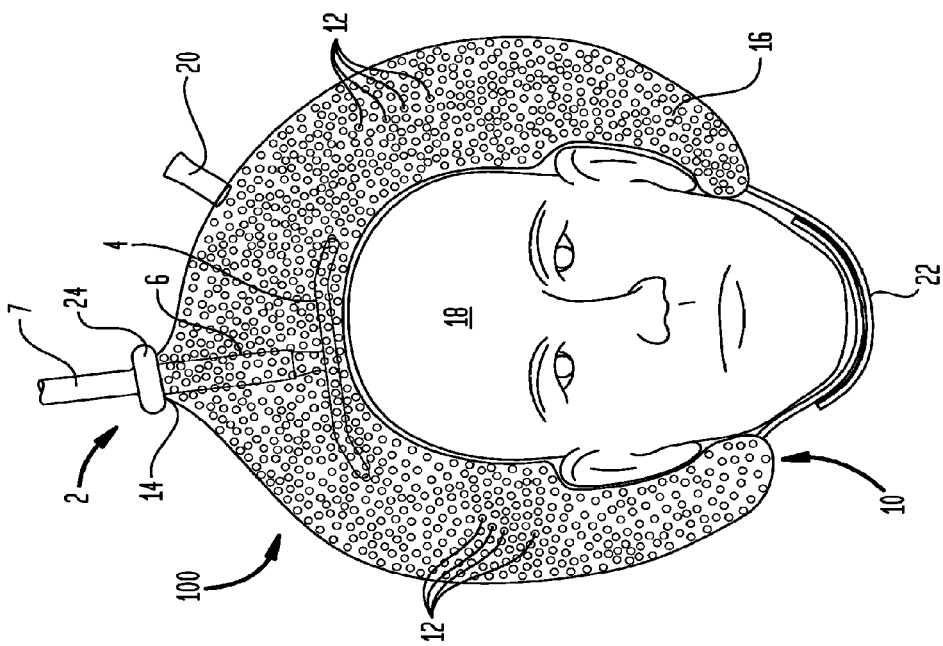

SECURING A TMS COIL TO THE PATIENT'S HEAD

STATEMENT REGARDING FEDERALLY SPONSORED RESEARCH OR DEVELOPMENT

This invention was made with government support under CTSA grant UL1 TR000064 awarded by the National Institutes of Health and the National Center for Research Resources. The government has certain rights in the invention.

BACKGROUND OF THE INVENTION

The invention relates to transcranial magnetic stimulation (TMS), and more particularly relates to TMS coils. In its most immediate sense, the invention relates to securing a TMS coil to a patient's head.

In TMS, a current pulse (or a series of current pulses) is directed through a coil (a "TMS coil") that is positioned adjacent the head of a human patient. Each current pulse causes the TMS coil to produce an intense magnetic field. This magnetic field induces changes in the state of polarization of neurons in the patient's brain, which changes in turn evoke activity in the brain. Measurement of this activity makes it possible to e.g. determine the functions of particular brain regions and to form a functional map of the brain.

A TMS study of a patient is carried out in two steps. In the first step, the TMS coil is targeted to the brain region of interest. Once this targeting has been accomplished, the actual study of the brain region is carried out by directing a series of pulses to the targeted region.

Conventionally, these steps are carried out with the technician holding the TMS coil in position. This is problematic because the TMS coil and its attached cable weigh approximately 9 pounds (approximately 4 kilograms) and the technician is challenged to keep the TMS coil properly targeted, i.e. properly located on the patient's head and properly oriented towards the brain region of interest. Additionally, it can be difficult for the technician to maintain such proper location and orientation when the patient's head moves.

Holders for TMS coils are known. These fix the position of the TMS coil in space, thereby eliminating problems associated with technician fatigue. However, such devices do not address the problems caused by movement of the patient's head. Furthermore, such devices do not facilitate repositioning of the TMS coil on the patient's head.

SUMMARY OF THE INVENTION

In accordance with the invention, a helmet is provided for removably securing a TMS coil having an attached handle to the patient's head. The helmet has a flexible and airtight sack, the sack having an interior volume and a centrally located opening, with the opening being sized to receive a TMS coil handle that is inserted into the sack. A valve is located on the sack, allowing air to be withdrawn from, and introduced into, the interior volume of the sack. A multiplicity of beads are located in the interior of the sack.

The handle of the TMS coil is inserted into the sack and the TMS coil is then placed at the appropriate location on the patient's head and oriented along the desired direction. A vacuum hose is used to withdraw air from the sack, causing the sack to shrink and causing the beads to form a compacted mass that presses against, and conforms to, the shape of the patient's head. As long as the vacuum is maintained, the helmet retains its conforming shape, which in turn keeps the TMS coil in the desired position and orientation. If the initial positioning and orientation of the TMS coil are not as desired, the vacuum is released. This allows air to enter the sack, un-compacting the beads and permitting the TMS coil to be repositioned and reoriented. Once such repositioning and reorientation has taken place, a vacuum hose is used once more to withdraw air from the sack. The beads are thereby re-compacted into a mass that conforms to the helmet's new location on the patient's head, and as long as the vacuum is maintained the helmet sack is maintained in its new shape for as long as necessary.

Advantageously, a support structure is provided, and means are provided for detachably suspending the handle of the TMS coil from the support structure. By doing so, the patient does not have to bear the weight of the TMS coil and cable. Furthermore, this reduces the physical effort required of the technician, because the technician does not need to hold the helmet against the patient's head. Also advantageously, a treadmill or chair may be provided, with the support structure supporting the helmet above the treadmill or chair as the case may be. Supporting the helmet above the treadmill makes it convenient to conduct a TMS study while the patient is exercising, and suspending the helmet above a chair makes it convenient to conduct a TMS study while the patient is resting. And, in each of these studies, the patient does not need to support the weight of the helmet, the TMS coil, and the electrical cable that connects the TMS coil to its associated electronic apparatus.

BRIEF DESCRIPTION OF THE DRAWINGS

The invention will be better understood with reference to the following illustrative and non-limiting drawings, in which:

FIG. 2 schematically illustrates a first preferred embodiment of apparatus in accordance with the invention;

FIG. 3 schematically illustrates a second preferred embodiment of apparatus in accordance with the invention;

DETAILED DESCRIPTION OF PREFERRED EMBODIMENTS

Figure 1:
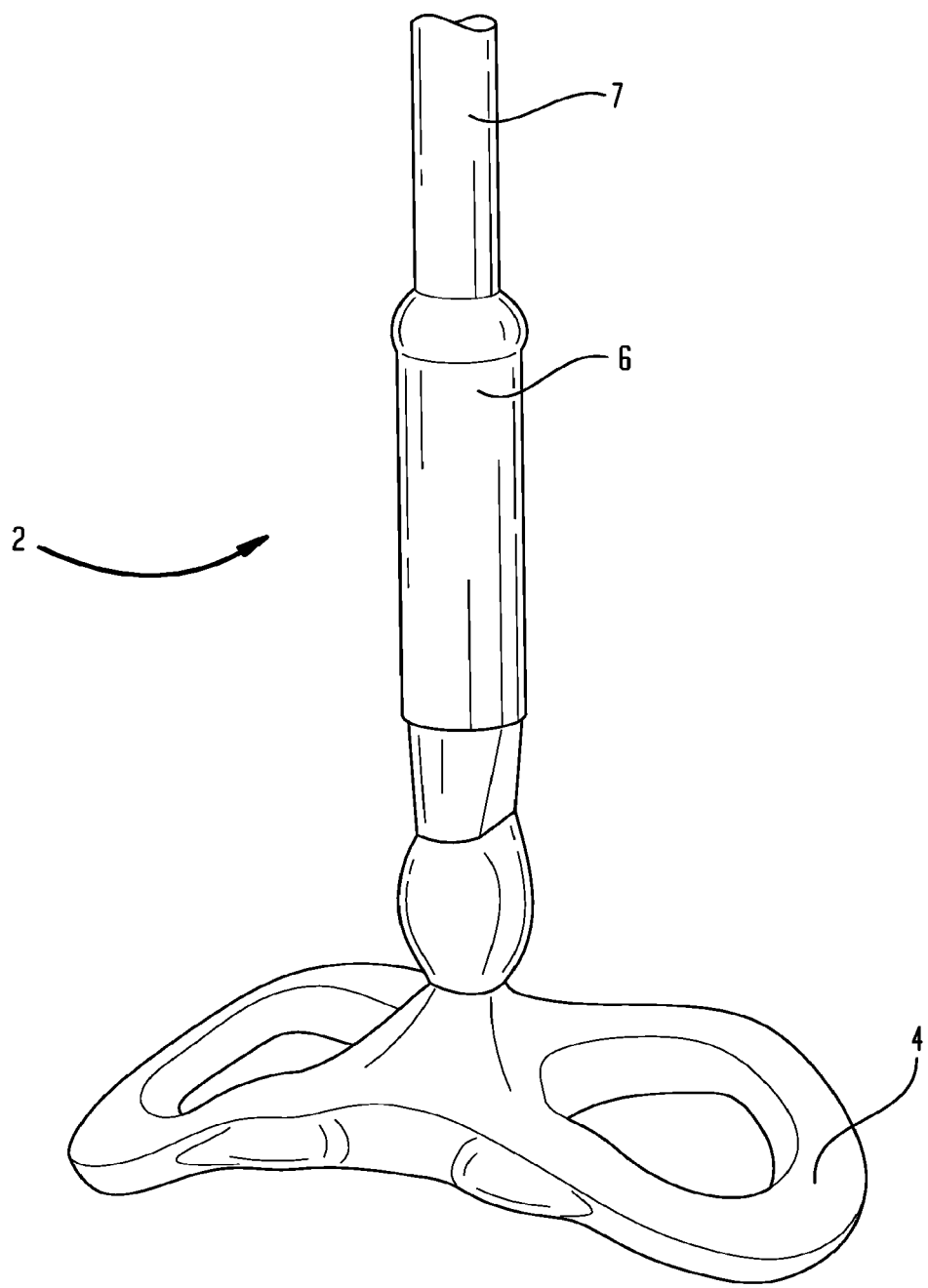
FIG. 1 schematically illustrates a TMS coil.
Figure 4:
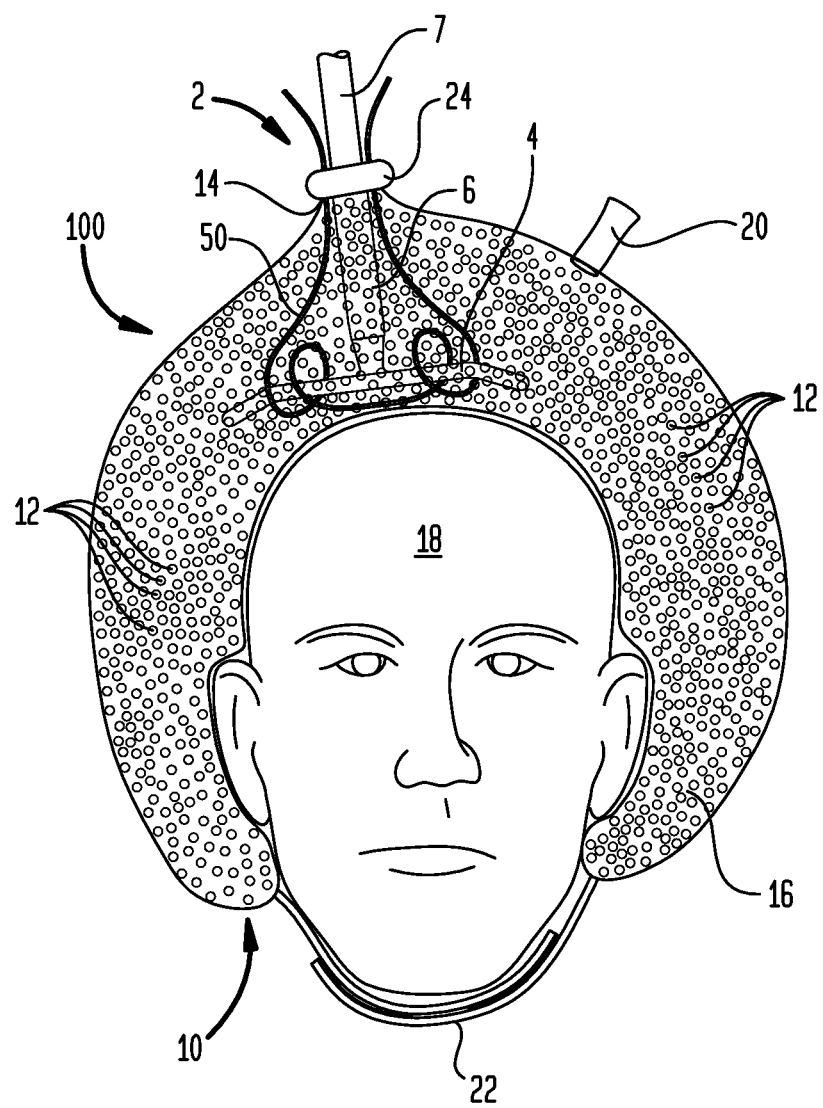
FIG. 4 schematically illustrates an optional feature that can be used with apparatus in accordance with the invention, shown used with the first preferred embodiment of apparatus in accordance with the invention.

In the Figures, the same element is always indicated by the same reference numeral. The Figures are not to scale, and details may be enlarged or eliminated for clarity. Corresponding elements in the various embodiments are indicated using primed reference numerals.

FIG. 1 shows a conventional TMS coil 2, having an antenna 4 at one end. An electric cable 7 is connectable to the handle 6 of the TMS coil 2. A TMS study of a patient (not shown in FIG. 1) is carried out by appropriately positioning and orienting the antenna 4 with respect to the head of the patient, directing current pulses through the antenna 4, and detecting and mapping the brain activity that is evoked.

FIG. 2 shows a first preferred embodiment of the invention. A helmet generally indicated by reference numeral 100 has a flexible and airtight sack 10, which may be made of nylon or any other material that can withstand repeated cleaning. The material used for the sack 10 is not part of the invention. The interior volume 16 of the sack is filled with a multiplicity of tiny beads 12, which are advantageously made of ⅛ inch polystyrene but can be made of any material that can withstand repeated cleaning. The size and composition of the beads 12 is not part of the invention. As shown, the sack 10 is shaped to leave the patient's face exposed but to otherwise surround the skull and to anchor at the patient's occiput.

An opening 14 in the sack 10 is sufficiently large to permit the antenna 4 of a TMS coil 2 to be introduced into the interior volume 16 of the sack 10, with the handle 6 of the TMS coil 2 projecting out of the opening 14. A seal 24 establishes an airtight seal between the handle 6 and the sack 10. A valve 20 permits air to be introduced into, and withdrawn from, the interior volume 16 of the sack 10.

In use, the antenna 4 of the TMS coil 2 is introduced into the interior volume 16 of sack 10 so that the antenna 4 is below the beads 12 at the bottom of the sack 10 and the handle 6 of the TMS coil 2 extends out of the opening 14. The seal 24 is then applied to create an airtight seal so that air can neither enter into, nor escape from, the opening 14. While the valve 20 is open, the sack 10 is placed on the patient's head 18 and one or more chin straps 22 is/are closed below the patient's chin to secure the helmet 100 to the patient's head 18. Advantageously, each of the chin straps 22 is of VELCRO, but this is not necessary. The way in which each of the chin straps 22 closes (i.e. VELCRO, buckle, etc.) is not a part of the invention.

The technician (not shown) then preliminarily positions and orients the TMS coil 2 to the desired location and orientation on the patient's head 18. Thereafter, air is withdrawn from the interior volume 16 via a vacuum hose (not shown) attached to the valve 20. This causes the sack 10 to shrink and to force the beads 12 into a rigid compacted mass that conforms to the shape of the patient's head 18. If the sack 10 is sufficiently airtight to prevent air leakage through the sack 10 into the interior volume 16, the sack 10, beads 12, and TMS coil 2 can be held fixed relative to each other merely by closing the valve 20. Alternatively, if the sack 10 is not airtight, the valve 20 can be kept open while the vacuum is maintained. As long as the beads 12 are held in a rigid compacted mass, the helmet 100 is prevented from moving with respect to the patient's head 18.

A pilot TMS study is then carried out to determine whether the TMS coil 2 is properly positioned and oriented. If so, the intended TMS study is then carried out. If not, air is readmitted into the interior volume 16 of the sack 10, whether by opening the valve 20 or by disconnecting the vacuum. This allows the sack 10 to expand, which frees the beads 12 to move and makes it possible for the technician to easily reposition and reorient the TMS coil 2 and helmet 100. Thereafter, air is once again withdrawn through the valve 20 and the sack 10 fixed in position on the patient's head 18. This process can be repeated as many times as necessary until the TMS coil 2 has been properly positioned, and the desired TMS study can then be carried out.

The second preferred embodiment of the invention shown in FIG. 3 shows a helmet generally indicated by reference numeral 200. With the exception of the sack 10', the openings 14a' and 14b', and the seals 24a' and 24b', all the elements of the helmet 200 are identical to those of the helmet 100 shown in FIG. 2. In this second preferred embodiment, the antenna 4 is not located within the interior volume 16' of the sack 10'. Rather, the sack 10 has two openings 14a' and 14b' through which the handle 6 of the TMS coil 2 extends, so that the antenna 4 is placed directly against the head 18 of the patient. Each of the openings 14a' and 14b' is sealed by a seal 24a' or 24b' to prevent air entering or leaving the interior volume 16' of the sack 10'. The operation of this second preferred embodiment illustrated in FIG. 3 is the same as the operation of the first preferred embodiment illustrated in FIG. 2.

During use, the antenna 4 can get hot. Optionally, to prevent overheating, a hollow fluid-tight tube 50 can be provided. The tube 50 is wrapped around the antenna 4 and both ends of the tube 50 exit the sack 10 or 10' through the opening 14 or openings 14a' and 14b'. Coolant such as ice water can then be directed through the tube 50 to cool the antenna 4 while the TMS coil 2 is in use.

Figure 5:
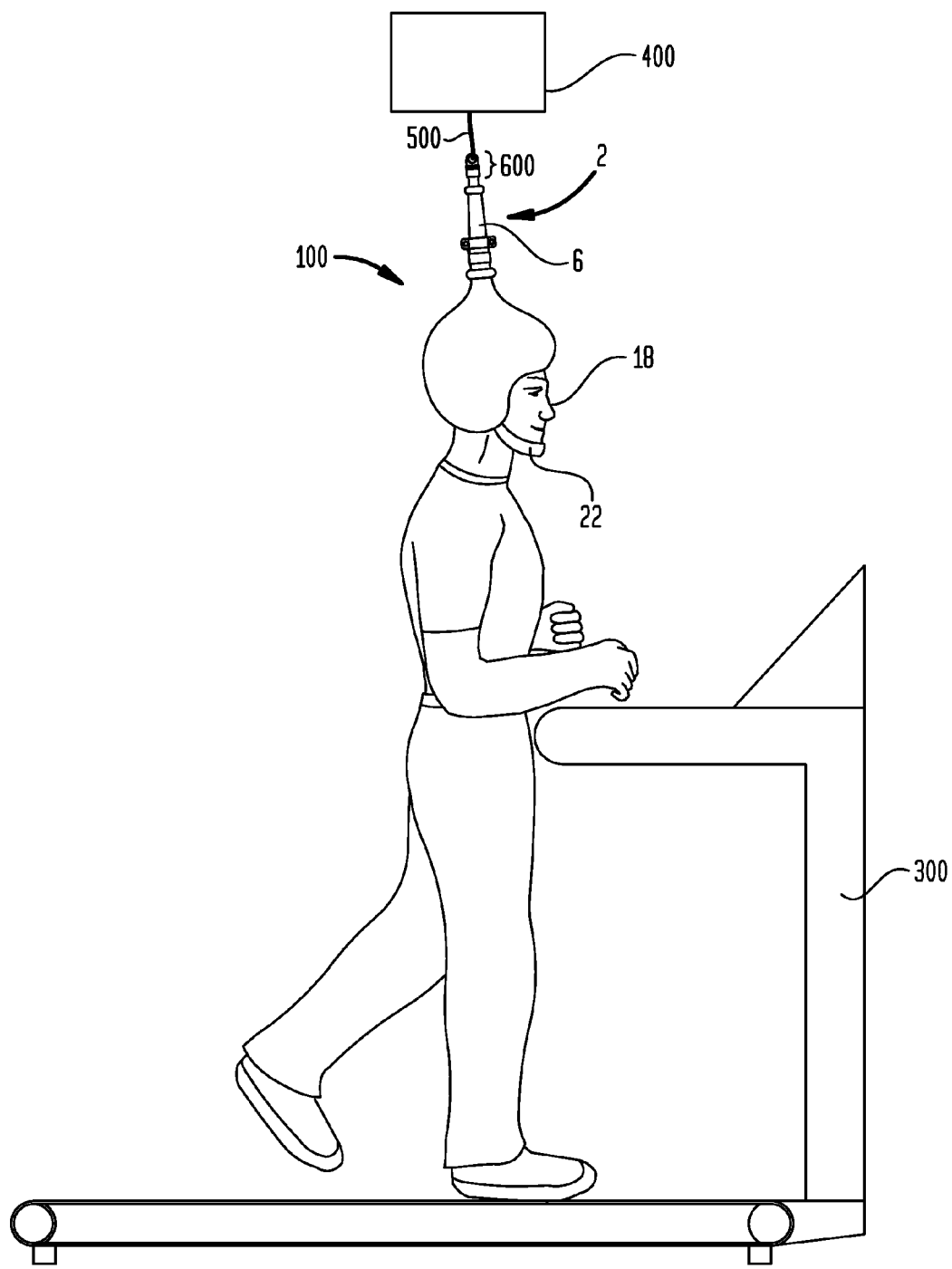
FIG. 5 schematically illustrates a preferred embodiment of the invention that facilitates a TMS study of an exercising patient.

TMS studies are also conducted on patients during exercise. As is shown in FIG. 5, a treadmill 300 is used to exercise the patient. A support 400 is provided, and the helmet 100 or 200 is suspended therefrom above the treadmill 300. As shown, this is accomplished by detachably connecting the handle 6 of the TMS coil 2 to the support 400. Advantageously, this detachable connection is accomplished by using a cable 500 and a breakaway assembly 600; the breakaway assembly 600 is designed to come apart if the force on the cable 500 exceeds approximately twice the weight of the helmet 100 or 200 with the TMS coil 2 mounted therein. In this embodiment, the breakaway assembly 600 uses mating VELCRO patches, but this is not required; the way in which the breakaway assembly 600 works is not part of the invention.

Figure 6:
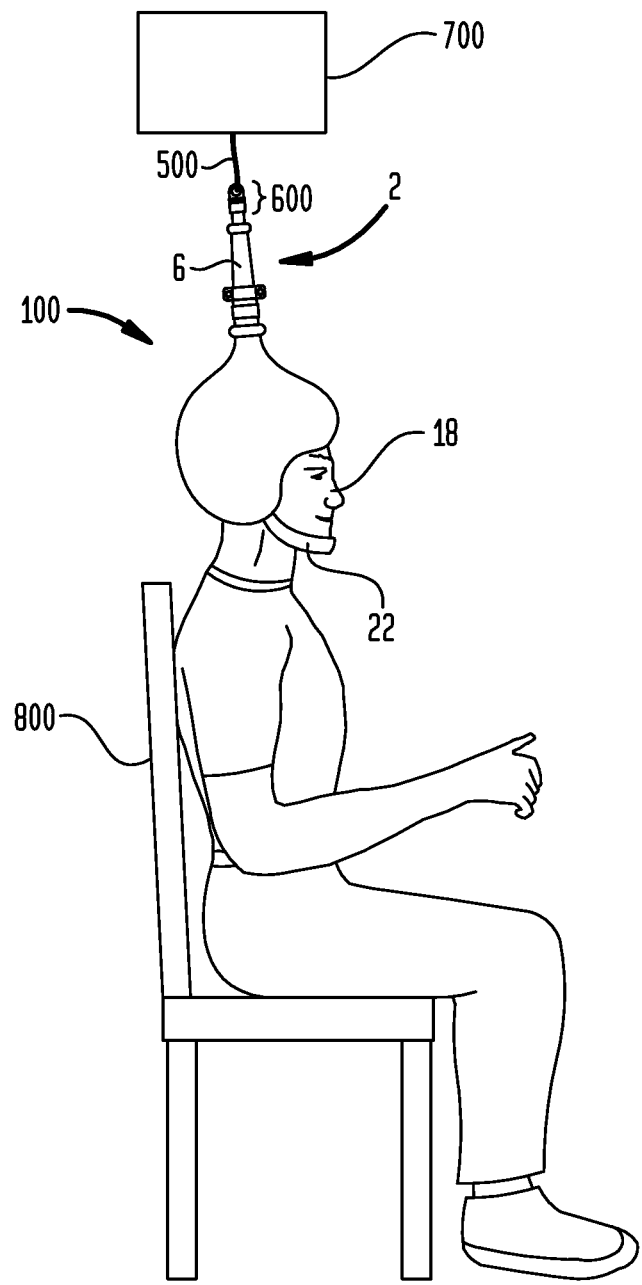
FIG. 6 schematically illustrates a preferred embodiment of the invention that facilitates a TMS study of a resting patient.

TMS studies are also conducted on patients that are seated. To make it unnecessary for the technician to hold the helmet 100 or 200, and for the patient to bear the weight of the helmet 100 or 200 on his or her head, a support 700 is used to suspend the helmet 100 or 200 above a chair 800 (see FIG. 6).

Although at least one preferred embodiment of the invention has been described above, this description is not limiting and is only exemplary. The scope of the invention is defined only by the claims, which follow:

The invention claimed is:

1. A helmet for removably attaching a TMS coil to a head of a living patient, the TMS coil having a handle, and the helmet comprising:
    a sack that is flexible and airtight, the sack having an interior volume and a centrally located opening, the opening being sized to receive a handle of the TMS coil that is inserted into the sack;
    a valve located on the sack, the valve allowing air to be withdrawn from, and introduced into, the interior volume of the sack; and
    a multiplicity of beads located in the interior volume of the sack,
    wherein the helmet is suspended from a support structure via a breakaway assembly that detachably engages the handle of the TMS coil that is inserted into the sack of the helmet;
    wherein said breakaway assembly is configured to detachably suspend the handle of the TMS coil from a support cable secured to the support structure when force on the support cable does not exceed twice the weight of the helmet with the TMS coil located therein and with the support cable connected to the TMS coil; and
    wherein said breakaway assembly is configured to detach the TMS coil from the support structure when force on the support cable exceeds twice the weight of the helmet with the TMS coil located therein and with the support cable connected to the TMS coil.

2. The helmet of claim 1, further comprising a chin strap.

3. The helmet of claim 1, wherein the sack is made of nylon and the beads are made of polystyrene.

4. The helmet of claim 1, wherein the opening is sized to receive a TMS coil and attached handle that are inserted into the interior volume of the sack, and further comprising means for creating an airtight seal between the sack and the handle.

5. The helmet of claim 1, further comprising means for cooling the TMS coil.

6. The helmet of claim 5, wherein the means for cooling comprises a hollow tube through which liquid coolant can be directed.

7. The helmet of claim 1, further comprising a chin strap.

8. The helmet of claim 1, wherein the sack is shaped to fit over a patient's head with the patient's face exposed.

9. The helmet of claim 8, wherein the sack is shaped to cover all regions of the patient's head except the patient's face and to anchor at the patient's occiput.

10. A system for removably attaching a TMS coil to a head of a living patient, the TMS coil having a handle, and the system comprising:
  a. a helmet, the helmet comprising:
    i. a flexible and airtight sack, the sack having an interior volume and a centrally located opening, the opening being sized to receive a TMS coil handle that is inserted into the sack;
    ii. a valve located on the sack, the valve allowing air to be withdrawn from, and introduced into, the interior volume of the sack, and
    iii. a multiplicity of beads located in the interior volume of the sack;
  b. a support structure; and
  c. a breakaway assembly for detachably suspending the handle of the TMS coil from the support structure;
  wherein said breakaway assembly is configured to detachably suspend the handle of the TMS coil from a support cable secured to the support structure when force on the support cable does not exceed twice the weight of the helmet with the TMS coil located therein and with the support cable connected to the TMS coil; and
  wherein said breakaway assembly is configured to detach the TMS coil from the support structure when force on the support cable exceeds twice the weight of the helmet with the TMS coil located therein and with the support cable connected to the TMS coil.

11. The system of claim 10, wherein the opening is sized to receive a TMS coil antenna and handle that are inserted into the interior volume of the sack, and further comprising a seal configured for creating an airtight seal between the sack and the handle.

12. The system of claim 10, further comprising a treadmill, the support structure being located to suspend the helmet above the treadmill.

13. The system of claim 10, further comprising a chair, the support structure being located to suspend the helmet above the chair.

14. The system of claim 10, further comprising a body strap.

* * * * *